United States Patent [19]

Atkinson et al.

[11] Patent Number: 5,409,471
[45] Date of Patent: Apr. 25, 1995

[54] METHOD OF LUBRICATING A MEDICAL COUPLING SITE

[75] Inventors: Gordon E. Atkinson, Cedarville; Frank J. BeaFore, Xenia, both of Ohio

[73] Assignee: Vernay Laboratories, Inc., Yellow Springs, Ohio

[21] Appl. No.: 85,740

[22] Filed: Jul. 6, 1993

[51] Int. Cl.⁶ .............................................. A61M 35/00
[52] U.S. Cl. ...................................... 604/289; 604/905
[58] Field of Search .............................. 604/289, 905

[56] References Cited

U.S. PATENT DOCUMENTS

| | | |
|---|---|---|
| 3,903,882 | 9/1975 | August . |
| 3,912,667 | 10/1975 | Spitzer et al. ............. 604/289 X |
| 4,117,187 | 9/1978 | Adams et al. ............. 428/286 |
| 4,263,363 | 4/1981 | Buck et al. ............. 428/284 |
| 4,281,650 | 8/1981 | Spiegelberg . |
| 4,326,569 | 4/1982 | Vaillencourt ............. 141/383 |
| 4,363,319 | 12/1982 | Altshules . |
| 4,427,111 | 1/1984 | Loipply ............. 206/210 |
| 4,427,115 | 1/1984 | Loipply ............. 206/484 |
| 4,557,381 | 2/1985 | Whitney ............. 206/440 |
| 4,588,400 | 5/1986 | Ring et al. ............. 604/304 |
| 4,627,936 | 12/1986 | Gould et al. ............. 252/558 |
| 4,657,534 | 4/1987 | Beck et al. ............. 604/184 X |
| 4,696,393 | 9/1987 | Laipply ............. 206/210 |
| 4,781,974 | 11/1988 | Bouchette et al. ............. 428/288 |
| 4,838,253 | 6/1989 | Brassington et al. . |
| 4,998,984 | 3/1991 | McClandon ............. 206/205 |
| 5,006,114 | 4/1991 | Rogers et al. ............. 604/167 |
| 5,009,652 | 4/1991 | Moyan et al. ............. 604/385 |
| 5,078,692 | 1/1992 | Cuprae ............. 604/192 |
| 5,141,803 | 8/1992 | Pregozen ............. 428/288 |
| 5,203,775 | 4/1993 | Frank et al. ............. 604/905 X |
| 5,251,873 | 10/1993 | Atkinson et al. ............. 604/905 X |
| 5,295,657 | 3/1994 | Atkinson ............. 604/905 X |
| 5,295,658 | 3/1994 | Atkinson et al. ............. 604/905 X |

OTHER PUBLICATIONS

The United States Pharmocopeia, Twentieth Revision, Jul. 1, 1980, p. 429.

Primary Examiner—Randall L. Green
Assistant Examiner—Mary Beth Jones
Attorney, Agent, or Firm—Biebel & French

[57] ABSTRACT

A method and apparatus for simultaneously sterilizing and lubricating a medical coupling site prior to insertion of a male luer into the site. A fiber pad is provided containing a liquid composition including a sterilizing agent and a lubricating agent. The sterilizing and lubricating agents are preferably isopropyl alcohol and silicone oil, respectively, such that application of the lubricating agent to the medical coupling site results in the alcohol evaporating to leave behind a coating of silicone oil. The silicone oil lubricates an area on the coupling site contacted by the end of a male luer.

10 Claims, 2 Drawing Sheets

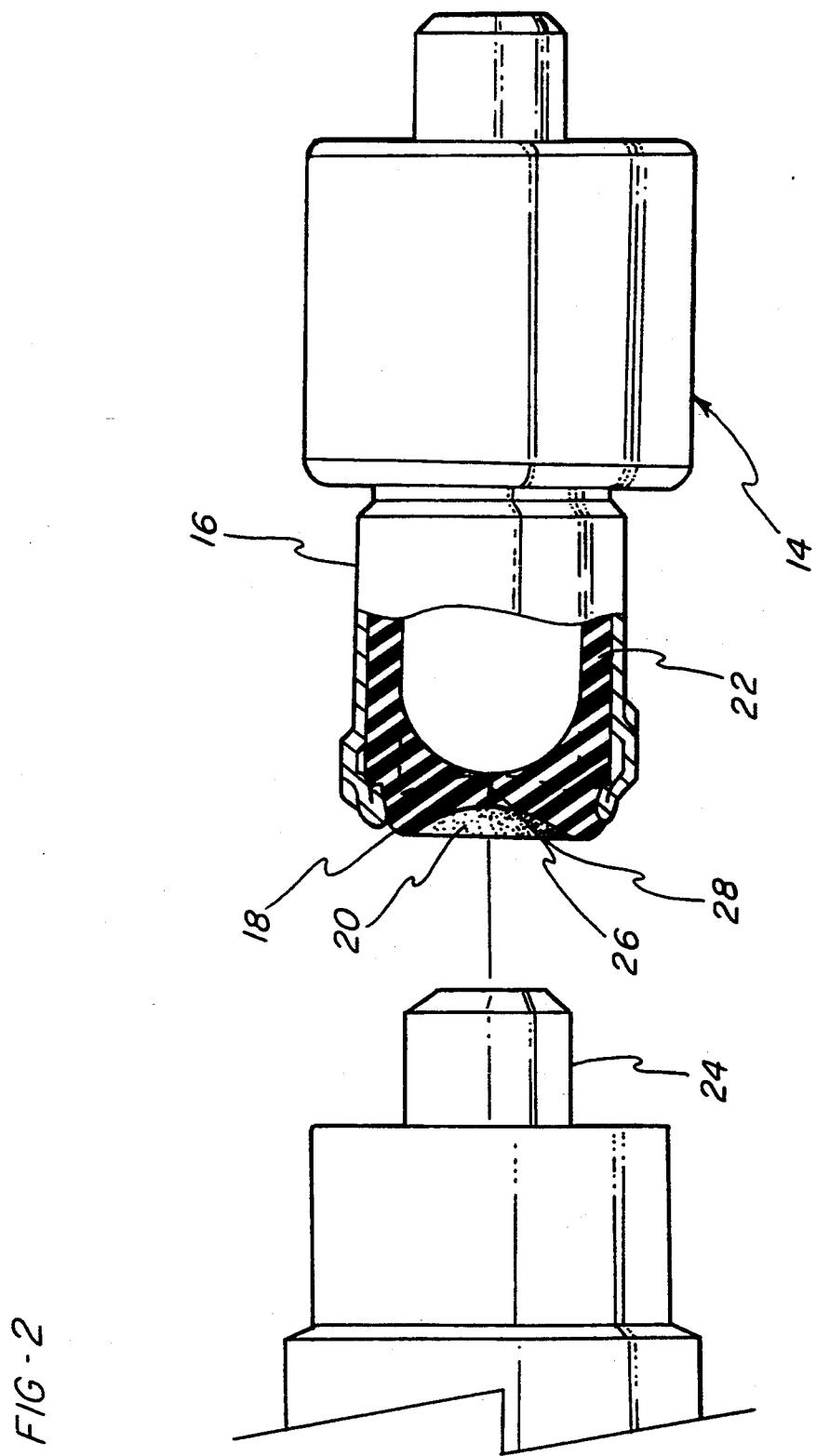

METHOD OF LUBRICATING A MEDICAL COUPLING SITE

BACKGROUND OF THE INVENTION

The present invention relates to lubrication of medical coupling sites and, more particularly, to a method and apparatus for sterilizing and lubricating a medical coupling site prior to insertion of a male luer into the site.

Medical coupling sites are commonly used to provide a quick and easy to access opening for dispensing fluids into an intravenous line. Medical coupling sites typically include an outer housing formed of plastic or other rigid material and a septum or valve element formed of rubber or some other elastomeric material supported within the housing. For example, U.S. Pat. No. 5,251,873 assigned to the assignee of the present invention, discloses a medical coupling site including a tubular valve element having a diaphragm with a slit formed therein for receiving a male luer. In addition, the tubular valve element is supported by a rigid retainer or housing defining the outer wall of the coupling site.

The procedure followed by medical personnel during insertion of a male luer through the diaphragm includes first wiping the coupling site with a wipe containing a sterilizing agent, such as isopropyl alcohol, prior to insertion of the male luer. Subsequently, the blunt end of the male luer is engaged against the outer surface of the diaphragm forcing the diaphragm to stretch and the slit to open a sufficient extent to permit passage of the male luer. Repeated wipings of the diaphragm with the sterilizing agent results in any lubricating substances present in the elastomeric valve being removed. Consequently, the frictional force between the end of the male luer and the diaphragm surface progressively increases as more and more of the lubricating substances are removed during repeated wipes of the diaphragm with the sterilizing agent.

Accordingly, the insertion force required for inserting the male luer into the medical coupling site increases as the lubricating substances on the diaphragm surface are depleted. Further, as a result of the increased friction between the male luer and the diaphragm, the diaphragm will tend to stick to the male luer during the insertion process such that the luer tip will tend to push the end of the valve inwardly into the coupling site and away from the housing rather than sliding across the diaphragm toward the slit to thereby stretch the diaphragm and open the slit for reception of the male luer tip.

Thus, it is apparent that there is a need for a method by which the elastomeric portion of a medical coupling site may be maintained in a lubricated state whereby insertion of a male luer through the medical coupling site is facilitated. In addition, there is a need for providing such a method without introducing any additional steps to the current procedure for preparing the coupling site to receive a male luer.

SUMMARY OF THE INVENTION

In order to facilitate insertion of a male luer into a medical coupling site, the present invention provides a method for lubricating a coupling site including the steps of providing a lubricating pad containing a liquid composition comprising a sterilizing agent and a lubricating agent, and wiping the site with the pad whereby the site is simultaneously sterilized and lubricated.

The pad preferably is provided in a sealed packet to form a package containing an individual pad such that the package may be opened and the pad removed just prior to use in wiping the site. After the site is wiped with the lubricating pad, the sterilizing agent evaporates and the lubricating agent is left behind as a coating on the site for facilitating movement of the end of a male luer across the diaphragm as the male luer is inserted through the site.

It is therefore a primary object of the present invention to provide a lubricating pad and a method for using the pad wherein the pad may be used in a procedure for preparing a medical coupling site to receive a male luer.

It is a further object of the present invention to provide such a lubricating pad wherein the pad includes a sterilizing agent and a lubricating agent whereby a lubricating coating is left on a surface of the medical coupling site for engaging a male luer to thereby facilitate insertion of the luer into the site.

Other objects and advantages of the invention will be apparent from the following description, the accompanying drawings, and the appended claims.

BRIEF DESCRIPTION OF THE DRAWINGS

FIG. 2 illustrates a medical coupling site in partial cut-away section which has been wiped with a lubricating pad of the present invention prior to insertion of a male luer.

DETAILED DESCRIPTION OF THE PREFERRED EMBODIMENT

Figure 1:
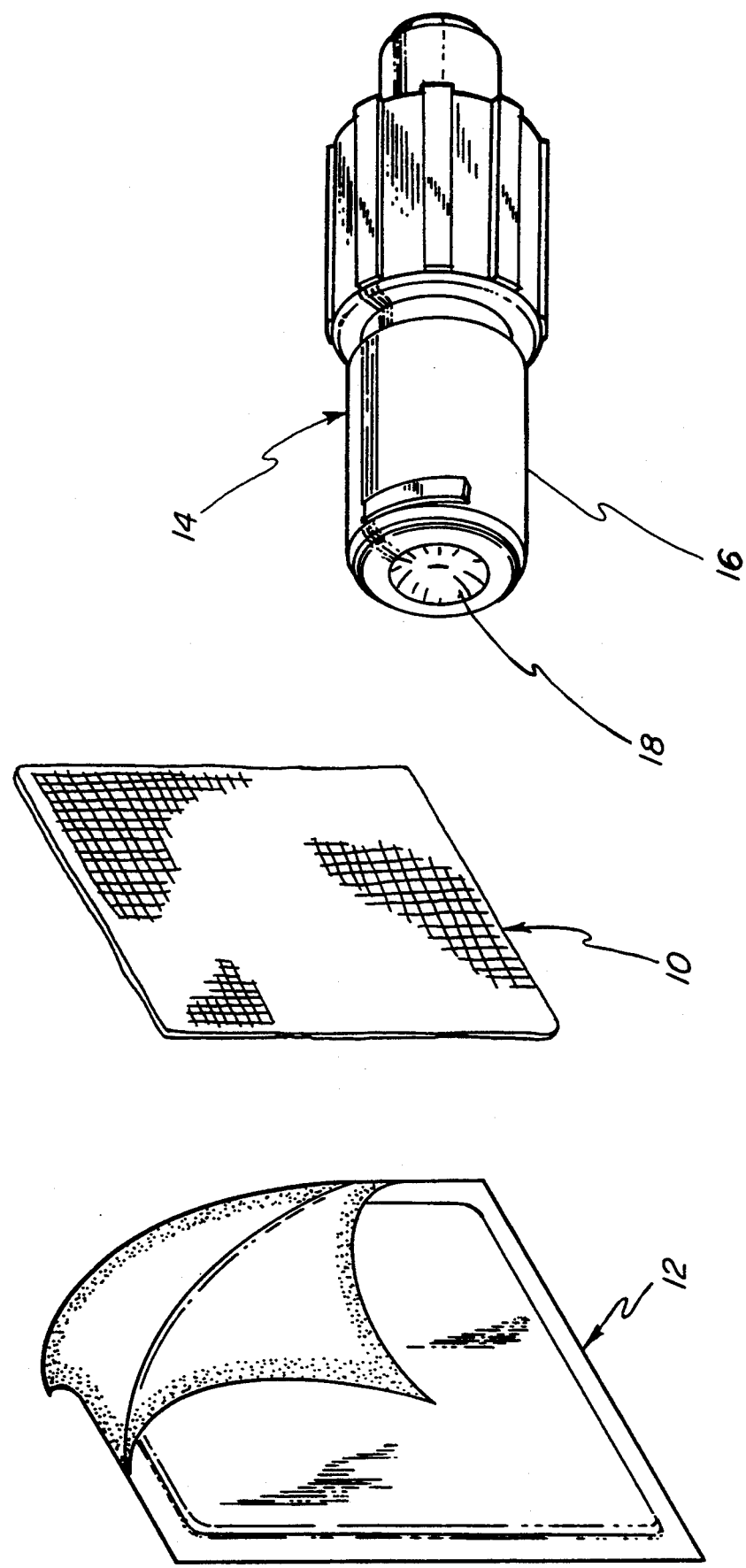
FIG. 1 illustrates a lubricating pad package of the present invention in its use for wiping a medical coupling site.

The present invention relates to providing a method for lubricating a medical coupling site and to an article or apparatus for carrying out the method. In particular, the present invention is directed toward a lubricated pad and a method for using the pad to wipe a resilient valve element of a medical coupling site whereby the valve element is sufficiently lubricated to facilitate insertion of a male luer into the site.

Referring to FIG. 1, the article for carrying out the invention includes a lubricating pad 10 and a foil packet 12 for containing the pad 10. The pad 10 is preferably a fiber pad and is adapted to receive a liquid composition comprising a sterilizing agent and a lubricating agent. Specifically, the pad 10 preferably contains a liquid composition which comprises silicone oil and an alcohol solution wherein the alcohol solution includes approximately 70% isopropyl alcohol and 30% distilled water by volume. The silicone oil and isopropyl alcohol solution are combined in a ratio which is within the range of from 1:2 to 1:20, silicone oil to alcohol solution, by volume. Each individual lubricating pad 10 is sterilized and placed in a respective packet 12 which is then sealed to form a package adapted to be stored for future use.

The present invention is particularly adapted to be used with a medical coupling site 14 having a rigid outer housing 16 forming a supporting sleeve member for a resilient valve element 18. Such a medical coupling site is disclosed in U.S. patent application Ser. No. 07/893,813, filed Jun. 6, 1992 and assigned to the assignee of the present invention, which application is incorporated herein by reference.

As may be further seen in FIG. 2, the valve element 18 disclosed in the above-noted application includes a diaphragm 20 extending diametrically across a tubular body portion 22. It should be apparent that as a male luer 24, such as the luer tip of a syringe or any other blunt cannula, is inserted through a slit 26 formed in the diaphragm, it is necessary for the sides of the luer 24 to slide past the outer surface of the diaphragm 20. Further, it should be apparent that should excessive friction develop between the outer surface of the diaphragm 20 and the outer surface of the luer 24, the luer 24 will tend to pull the diaphragm with it as the luer 24 proceeds through the tubular body 22, which could result in destruction of the coupling site 14. In addition, excessive friction also results in the production of unacceptable insertion forces being required to push the luer 24 past the diaphragm 20.

In the use of the present invention, the lubricated pad 10 is wiped across the outer surface of the diaphragm 20 leaving a coating 28 of alcohol and silicone oil on the diaphragm 20. Subsequently, the alcohol evaporates leaving the silicone oil as a lubricant for lubricating the surfaces contacted by the blunt end of the male luer 24. Thus, as the end of the luer 24 comes into engagement with the diaphragm 20, the end of the luer 24 will tend to slide along the coating 28 on the diaphragm surface and merely stretch the diaphragm open at the location of the slit 26 rather than developing forces which would tend to draw the diaphragm 20 inwardly through the coupling site 14.

Thus, it should be apparent that the present invention provides a method and apparatus for lubricating a medical site whereby the procedure for lubricating the site does not require medical personnel to perform any additional steps beyond the established procedure for sterilizing a medical coupling site prior to insertion of a male luer. Further, the present invention is carried out by the provision of a unique pad containing both a sterilizing agent and a lubricating agent whereby a sterilizing and lubricating step may be performed simultaneously on the coupling site.

It should also be noted that although isopropyl alcohol and silicone oil are disclosed as the sterilizing and lubricating agents, respectively, other medical grade sterilizing and lubricating agents may also be used within the scope of the present invention.

While the method and form of apparatus herein described constitutes a preferred embodiment of this invention, it is to be understood that the invention is not limited to this precise method or form of apparatus, and that changes may be made therein without departing from the scope of the invention, which is defined in the appended claims.

What is claimed is:

1. A method of lubricating a medical coupling site including the steps of:
   providing a pad including a liquid composition comprising a sterilizing agent and a lubricating agent which is different from said sterilizing agent, and
   wiping said site with said pad whereby said site is simultaneously sterilized and lubricated.

2. The method as in claim 1 wherein said sterilizing agent comprises an isopropyl alcohol solution.

3. The method as in claim 2 wherein said lubricating agent comprises medical grade silicone oil.

4. The method as in claim 3 wherein said isopropyl alcohol solution comprises approximately 70% isopropyl alcohol and 30% distilled water by volume.

5. The method as in claim 4 wherein the ratio of said silicone oil to said isopropyl alcohol solution is in the range from 1:2 to 1:20 by volume.

6. The method as in claim 3 including the step of allowing said alcohol to evaporate while leaving said silicone oil as a lubricating coating on said site.

7. The method as in claim 1 further including the step of contacting the area wiped by said pad with a male luer during insertion of said luer through said site.

8. The method as in claim 1 wherein said step of providing said pad further includes the step of opening a sealed packet containing an individual pad and removing said pad from said package.

9. The method as in claim 1 wherein said sterilizing agent has a component which evaporates in air including the step of allowing said sterilizing agent to evaporate, leaving said lubricating agent on said site.

10. A method of lubricating a medical coupling site for receiving a male luer including the steps of:
    providing a pad including a liquid composition comprising a sterilizing agent having a component which evaporates in air and a lubricating agent which is different from said sterilizing agent,
    wiping said site with said pad, and
    allowing said sterilizing agent to evaporate, while leaving said lubricating agent on said site.

* * * * *